United States Patent [19]

Radici et al.

[11] Patent Number: 5,574,198
[45] Date of Patent: Nov. 12, 1996

[54] PROCESS FOR PRODUCING LINEAR ALKYLBENZENES

[75] Inventors: Pierino Radici, Turate; Pierluigi Cozzi, Nerviano; Giuseppe Giuffrida, Caronno Pertusella; Agostino Zatta, San Donato Milanese, all of Italy

[73] Assignee: Enichem Augusta S.p.A., Palermo, Italy

[21] Appl. No.: 419,959

[22] Filed: Apr. 10, 1995

Related U.S. Application Data

[63] Continuation of Ser. No. 124,060, Sep. 21, 1993, abandoned.

[30] Foreign Application Priority Data

Sep. 24, 1992 [IT] Italy .................................. MI92A2177

[51] Int. Cl.$^6$ ........................................................ C07C 2/68
[52] U.S. Cl. ........................ 585/323; 585/259; 585/446; 585/455; 585/459
[58] Field of Search ........................... 585/446, 455, 585/456, 459, 323, 658, 258, 259

[56] References Cited

U.S. PATENT DOCUMENTS

| | | | |
|---|---|---|---|
| 3,875,253 | 4/1975 | Huang | 585/660 |
| 4,520,214 | 5/1985 | Vora | 585/254 |

OTHER PUBLICATIONS

Chemical Abstract vol. 85, No. 1, 5 Jul. 1976, Abstract No. 5348j pp. 427–428.

*Primary Examiner*—Ponnathapura Achutamurthy
*Attorney, Agent, or Firm*—Spencer & Frank

[57] ABSTRACT

The present invention relates to an improved process for preparing linear alkylbenzenes falling within such range as used in detergency ($C_{10}$–$C_{14}$), which process consists of alkylating aromatic hydrocarbons (above all, benzene) with n-olefins in the presence of $AlCl_3$, wherein said n-olefins are obtained by dehydrogenating n-paraffins.

10 Claims, No Drawings

PROCESS FOR PRODUCING LINEAR ALKYLBENZENES

This is a continuation of application Ser. No. 08/124,060, filed on Sep. 21, 1993, now abandoned.

The present invention relates to an improved process for preparing linear alkylbenzenes falling within such range as used in detergency ($C_{10}$–$C_{14}$), which process consists of alkylating aromatic hydrocarbons (above all, benzene) with n-olefins in the presence of $AlCl_3$, with said n-olefins being obtained by dehydrogenating n-paraffins.

More particularly, the present invention relates to an integrated process of dehydrogenation of n-paraffins and subsequent reaction of the resulting mixture with aromatic hydrocarbons, with the latter being accomplished in the presence of $AlCl_3$, directly on the mixture deriving from the dehydrogenation.

Still more specifically, and in the case of benzene alkylation, the mixture of olefins and paraffins leaving the dehydrogenation reaction, after a preliminary separation of hydrogen and light hydrocarbons, is admixed with benzene and is sent to the alkylation zone together with the $AlCl_3$ based catalyst.

After leaving the alkylation unit, the mixture is allowed to decant in order to enable a complex of catalyst and hydrocarbons, substantially insoluble in the reaction mixture, to separate; said separated complex is partially recycled to the alkylation mixture.

The raw alkylated liquid is subsequently washed with acid solutions, such as, e.g., hydrochloric acid, or with a solution of sodium hydroxide and finally with water, before being sent to the distillation. In this step, the excess of benzene is first separated and recycled to the alkylation, and subsequently the excess of paraffins are separated together with small amounts of light aromatics. This stream, after make-up with fresh paraffins, is recycled to the dehydrogenation reactor.

The residual mixture of alkylated products is sent to a third distillation tower, in which linear alkylbenzene and the mixture of heavy alkylated species are obtained as the overhead and, respectively, the bottom streams; the latter can be partially recycled to the alkylation reactor.

Linear alkylbenzene can be used in order to be directly converted into benzene-sulfonic acid, or, according to a preferred embodiment, it may be first submitted to a purification treatment with $H_2SO_4$, or to a hydrogenation treatment in the presence of a nickel or noble metal-based supported catalyst. In that way, a sulfonic acid product is obtained which displays the best color characteristics even at high rations of $SO_3$: organic matter during the sulfonation step.

Recycling the paraffins coming from alkylation to the dehydrogenation reactor preferably requires a purification treatment over a material capable of removing any possible traces of organic chlorine present. An example of such a kind of product may be activated alumina. In that way, the active life time of the dehydrogenation catalyst is extended, with obvious financial advantages. Furthermore, the same selectivity of the dehydrogenation reaction is considerably improved. In fact, it is well known that during the reaction, besides normal monoolefins, also diolefins, aromatics and lower than $C_{10}$ cracking products are formed, which must be removed before the alkylation reaction. Furthermore, isomerization reactions take place, with iso-paraffins and iso-olefins being formed.

Besides the reaction conditions (LHSV, T, P and hydrogen:hydrocarbon ratio), the impurities are important, which are present in recycled n-paraffins. In fact, during the alkylations, reactions take place of olefin breakdown and of alkyl- and polyalkylbenzenes transalkylation, leading to the formation of products with aromatic character displaying a lower boiling point than of linear alkylbenzene.

The amounts and types of these light products are of basic importance as to the useful life time of the dehydrogenation catalyst. The use of $AlCl_3$-based catalyst in benzene alkylation processes leads, as compared to hydrofluoric acid, to a decrease in the contents of such light products in the recycled paraffins, with a consequent improvement in the economic balance as regards the useful life of the dehydrogenation catalyst and the selectivity of the latter.

The aromatic products, prevailing constituted by light alkylbenzenes, are less prone to undergo a cracking reaction on the dehydrogenation catalyst—which may also lead to carbon formation—than geminal diphenyls and light diphenylalkanes contained in paraffins coming from alkylation in the presence of HF.

All these products are added to those which are already contained in fresh paraffins and which are directly formed during the reaction of n-paraffin dehydrogenation: in any case, the average content of aromatic compounds present in recycled paraffins and consequently in the other streams leaving the dehydrogenation reactor, are lower.

The dehydrogenation is carried out according to well known procedures for those skilled in the art. Thus, the reaction is carried out in the presence of a catalyst comprising a noble metal, suitably supported on porous material: the catalyst basically comprises an element from platinum group at a level of from 0.01 to 2%, an alkali or alkaline-earth metal, at a level of from 0.1 to 5%; it may furthermore contain a component selected from one or more of the following:

tin from 0.1 to 1%, indium from 0.1 to 1%, thallium from 0.1 to 1%.

In those case when indium and thallium are simultaneously present, they are present in such amounts that In/Tl $\geq$ 0.3

Pt/(In+Tl) $\geq$ 1.5

Still according to the prior art, the dehydrogenation reaction is carried out at temperature comprised within the range of from 400° to 600° C., under a pressure comprised within the range of from 0.1 to 10 kg/cm2 and with a space velocity (LHSV) comprised within the range of from 0.1 to 100 $h^{-1}$; the ratio of hydrogen to paraffins is comprised within the range of from 0.5 to 20, by mol.

During the process of dehydrogenation of paraffins into olefins, not negligible amounts of diolefins are formed. On an absolute basis, their level depends on the conversion rate and on the conditions of the same process. Their presence leads subsequently, during the alkylation reaction, to the formation such impurities, such as tetralins in the alkylbenzene; and of high-boiling heavy products such as, e.g., diphenylalkanes and higher-molecular-weight tetralins and indanes. Therefore, selectively hydrogenating diolefins in order to convert them into monoolefins may prove advantageous in order to reduce the outlined drawbacks.

The hydrogenation is carried out on a stationary bed catalyst based on nickel supported on alumina, partially poisoned, or on a noble metal based catalyst such as palladium supported on carbon. In any case, the ratio of Hz:diolefins is kept higher than 1, and is generally comprised within the range of from 1.1:1 to 5:1, according to the catalyst and to the process conditions selected. Also the choice of the position of the different steps in the general scheme of the production process is important. In particulart the selective hydrogenation may be carried out upstream or downstream from the tower of separation of cracking products from olefin-paraffin mixture coming from the dehydrogenation step.

The reaction can be carried out at a temperature comprised within the range of from 50° to 250° C., according to the type of catalyst used and under a pressure comprised within the range of from 1 to kg/cm$^2$, while the space velocity of the liquid hydrocarbon stream may be comprised within the range of from 0.5 to 20 h$^{-1}$. In that way, yields of diolefin conversion of up to 100% are obtained with selectivity rates up to 90%.

The alkylation reaction is carried out after mixing the reactants (olefins in paraffin and benzene) inside the reactor, together with AlCl$_3$. According to a preferred embodiment, the fresh catalyst is added to the hydrocarbonaceous catalytic complex which is recycled and fed to the reactor.

The catalyst amount used is generally comprised within the range of from 0.05 to 10% by relatively to the olefin, and the molar ratio of benzene:olefin is comprised within the range of from 1:1 to 20:1, preferably of from 3:1 to 15:11. The reaction is generally carried out at a temperature comprised within the range of from 20° to 80° C., under a pressure comprised within the range of from 1 to 5 kg/cm$^2$ over times which usually range from 5 to 180 minutes.

The separation of the aluminum-chloride-based hydrocarbonaceous catalytic complex makes it possible that catalyst portion which is still active to be used again, and the catalytic activity to be kept constant by means of the addition of fresh AlCl$_3$. The addition of the latter to the complex catalyst causes a very active catalytic species to be formed. In fact, the presence of a heterogeneous catalytic phase makes it possible the reaction of transalkylation of polyalkylated species formed from the reaction of benzene with olefin to be activated, with high yields of Linear alkylbenzene being obtained and the residual alkylated products with higher molecular weight values to be decreased.

It is well known that AlCl$_3$ requires the presence of a cocatalyst to be transformed into an active species for alkylation. For that purpose, generally such compounds are used as water and/or hydrochloric acid, with different active species being obtained. According to a preferred embodiment, water is added in a regular mode by controlling the humidity in the reactants, in particular in benzene. The ratio of H$_2$O to AlCl$_3$ may be comprised within the range of from 1 to 100% by mol, and preferably of from 5 to 50%.

To the alkylation reactor, the high-boiling products recovered from the bottom of alkylbenzene distillation tower can be recycled. Their amount may be as high as about 50% of total weight of olefin charged together with the paraffin.

In that way, their recovery is favored with the transalkylation reaction being developed up to thermodynamic equilibrium.

The alkylbenzene [LAB] obtained according to the process of the present invention displays better characteristics in term of purity and overall linearity. The contents of cyclic compounds, such as dialkyl-tetralins and dialkyl-indanes are reduced to values lower than 2%, preferably lower than 1%, and the linear alkylbenzenes reach purity values higher than 95%. Such purity values reduce the need for burdensome process of subsequent purification by treatment with sulphuric acid in order to obtain end alkylbenzene sulfonates with light color and good stability over time.

Furthermore, the high contents of Linear alkylbenzenes also accelerates the subsequent biodegradation of the respective sulfonic acid in waste liquors. This is a very important feature, when one considers that more and more stringent rules for products which are as environmentally compatible as possible are being passed from day to day.

It should be finally observed that the high Level of 2-phenyl-isomers supplies sodium alkylbenzene sulfonate with high water solubility and good viscosity values, thus making it suitable for use above all in liquid detergent formulations.

The high-boiling products are prevailingly (>85%) constituted by polyalkylates having molecular weight >320, with a high fraction of dialkylates having molecular weight >360. These characteristics open wide application possibilities for use as high molecular weight sulfonic acid particularly used in the sector of lubrication. Their value is such as to transform a material which practically is a byproduct, into novel, high-added-value product.

EXAMPLE 1

A mixture, in gas phase, of normal C$_{10}$–C$_{13}$ paraffin and hydrogen in a molar ratio of 8 is sent to a tubular reactor containing a solid dehydrogenation catalyst as a 250-mm thick bed, kept at a temperature of 485° C. under a pressure of 2.0 kg/cm$^2$, with a hourly space velocity, evaluated on the liquid paraffin feedstock, of 21 h$^{-1}$ (volumes of liquid paraffin at 20° per catalyst volume per hour). The reactor Leaving mixture, after hydrogen and light products from cracking being separates, displays a content of olefin of 12.5%, with a bromine number of 12.11 (as determined according to the relevant ASTM method).

The analysis of the dehydrogenation mixture under steady-state conditions, carried out by HPLC, yields the following composition:

| | |
|---|---|
| paraffin = | 85.0% |
| monoolefin = | 11.9% |
| diolefin = | 0.6% |
| aromatics = | 2.5%. |

To such a mixture, benzene is added in a molar ratio of 8:1 relatively to the olefin content, and the resulting mixture is fed, together with a suspension of 10% anhydrous aluminum chloride in C$_{10}$–C$_{13}$ paraffin, to the bottom of an alkylation reaction. The temperatures of the feedstock streams are so adjusted as to realize a temperature of 55° C. inside the alkylation reactor.

The reactor used in this test has a cylindrical shape with a height/diameter ratio of 5:1, is equipped with a stirrer consisting of 5 turbines arranged at regular distances along the shaft and revolving at 150 rpm. It additionally is provided, inside its interior, with 4 separation baffles installed at regular distances between the blades, and provided with a central hole of 40% of inner reactor diameter, and with 4 vertical baffles installed along the wall of the reactor. An outern skirt for water circulation makes it possible the reactor to be precisely thermostatted at any desired temperatures.

After a one hour stay inside the reactor, the reaction mixture discharged from top reactor end and is allowed to decant inside a non-stirred cylindrical tank having a ratio of height to diameter of 5:1, and with such a capacity as to ensure a stay time of 45 minutes.

In that way, the separation of the hydrocarbonaceous catalytic complex is accomplished: a portion thereof is recycled in such an amount that inside the alkylation reactor approximately 6 parts by weight of such a product is present, with the residual portion being sent to disposal.

After being washed with an aqueous solution of HCl at 5% and subsequently with water inside two towers arranged cascade, the raw alkylated liquid is sent to the tower.

This process step is carried out inside three towers installed in cascade: inside the first and second towers, benzene and respectively paraffins and other light hydrocarbons are separated, and inside the third column an overhead stream of Linear alkylbenzene and a bottom stream of high-boiling alkylated products are recovered.

The paraffins separated in the second tower are recycled to the dehydrogenation reactor together with the topping-up paraffins. The high-boiling alkylated products are partially recycled to the alkylation reactor in such an amount that under steady-state conditions approximately 4 parts by weight is present.

When the whole process has reached its steady-state conditions, the composition of the stream fed to the dehydrogenation reactor is as follows:

| * paraffins | 69.3 parts by weight |
|---|---|
| * hydrogen | 13.73 parts by weight | wherein the paraffins are constituted as follows:

| $n\text{-}C_{10}$ = | 15.4% |
|---|---|
| $n\text{-}C_{11}$ = | 33.2% |
| $n\text{-}C_{12}$ = | 27.5% |
| $n\text{-}C_{13}$ = | 19.4% |
| $n\text{-}C_{14}$ = | 0.2% |
| branched hydrocarbons = | 4.3% | and the hydrogen stream is composed by:

| * $H_2$ = | 92.4% |
|---|---|
| * $C_1$ = | 1.61% |
| * $C_2$ = | 4.18% |
| * $C_3$ = | 1.65% |
| * $C_4$ = | 0.16%. |

The resulting linear alkylbenzene [LAB] product displays the following characteristicst as determined according to convectional techniques:

| Gas-chromatography | |
|---|---|
| <$n\text{-phenyl-}C_{10}$ = | 0.46% |
| $n\text{-phenyl-}C_{10}$ = | 14.81% |
| $n\text{-phenyl-}C_{11}$ = | 32.92% |
| $n\text{-phenyl-}C_{12}$ = | 28.83% |
| $n\text{-phenyl-}C_{13}$ = | 19.77% |
| $n\text{-phenyl-}C_{14}$ = | 0.20% |
| total $n\text{-phenyl-}C_{10}\text{-}C_{13}$'s = | 96.53% |
| dialkyl tetralins = | 0.75% |
| iso alkyl benzenes = | 2.26% |
| 2-phenylisomers = | 30.10% |
| bromine number = | 20 mg of Br/100 g |
| chlorine = | 8 ppm |

The heavy alkylated product separated by distillation displays the following characteristics:

| * Residual LAB: | 0.8% [1] |
|---|---|
| * Alkyl-polyalkylbenzenes = | 91.85% [2] |
| * Naphthalenes = | 2.60% [2] |
| * Dinaphthenebenzenes = | 0.58% [2] |
| * Tetralins, indanes = | 3.65% [2] |
| * Molecular weight: | 340.5 |
| * Gardner color = | 7. |

[1] as determined by gas-chromatography
[2] as determined by mass analysis

In an analogous way, the alkylation mixture is constituted as follows:

| * mixture from dehydrogenation reactor (8.44 parts of olefin) | 67.5 parts |
|---|---|
| * benzene | 32.5 parts |
| * $AlCl_3$ | 0.1 parts |
| * high-boiling alkylates | 4.0 parts |
| * Hydrocarbonaceous catalytic complex | 6.0 parts | wherein the total amount of water introduced together with the reactants is 0,002 parts.

Under steady-state conditions, the following results are obtained:

** Raw-materials per each 1000 parts of linear alkylbenzene [LAB]
865 parts of n-paraffin
350 parts of benzene
8 parts of $AlCl_3$
** Other products hydrogen and hydrocarbons: 65
heavy alkylates: 150 wherein the "n-paraffins" are constituted as follows:

| <$n\text{-}C_{10}$ = | 0.05% |
|---|---|
| $n\text{-}C_{10}$ = | 10.29% |
| $n\text{-}C_{11}$ = | 31.73% |
| $n\text{-}C_{12}$ = | 30.63% |
| $n\text{-}C_{13}$ = | 26.14% |
| >$n\text{-}C_{13}$ = | 0.60% |
| iso-paraffins = | 0.31% |
| aromatics = | 0.25% |

EXAMPLE 2

The same mixture coming from the dehydrogenation reactor and constituted by paraffins and 12.5% of olefin, used in Example 1, was sent to the alkylation reactor, so as to have, under steady-state conditions, at a temperature of 60° C., the following composition in the reactive system:

| * mixture from dehydrogenation reactor | 67.5 parts |
|---|---|
| * benzene | 32.5 parts |
| * $AlCl_3$ | 0.2 parts |
| * high-boiling alkylates | 4.0 parts |
| * hydrocarbonaceous catalytic complex | 8.0 parts | wherein the total amount of water added together with the reactants is 0.01 parts.

The linear alkylbenzene produced after the removal of benzene and paraffins according to the above disclosed methodology displays the following characteristics:

| $n\text{-phenyl-}C_{10}\text{-}C_{13}$'s = | 95.6% |
|---|---|
| tetralins = | 1.0% |

-continued

| | |
|---|---|
| iso alkyl benzenes = | 3.0% |
| 2-phenylisomers $C_{10}$–$C_{13}$ = | 29.8% |
| bromine number = | 22 (ASTM) |

The heavy alkylated product separated from the bottom of the distillation tower displays the following composition:

| | |
|---|---|
| * Residual LAB: | 2.1% [1] |
| * Alkyl-polyalkylbenzenes = | 86.5 [2] |
| * Diphenyl-alkane-acenaphthenes = | 5.0 [2] |
| * Naphthalenes = | 1.6 [2] |
| * Dinaphthenebenzenes = | 1.7 [2] |
| * Tetralins, indanes = | 5.2 [2] |
| * Molecular weight: | 361.3 |

[1] as determined by gas-chromatography
[2] as determined by mass analysis

Under steady-state conditions, the following results ar obtained:

| |
|---|
| ** raw materials per each 1000 parts of linear alkylbenzene [LAB] |
| 827 parts of paraffin |
| 335 parts of benzene |
| 15 parts of $AlCl_3$ |
| ** other products |
| hydrogen and light hydrocarbons: 65 |
| heavy alkylates: 96 |

EXAMPLE 3

The mixture of paraffins and olefins from the dehydrogenation reactor maintained under the same conditions as of Example 1 is submitted to a reaction of selective hydrogenation of the diolefins contained in it. The mixture having the same composition as is in indicated as of Example 1 admixed with hydrogen is a molar ratio, relatively to diolefins, of 1.15 and subsequently fed to a reactor containing a solid catalyst composed by 0.25% of palladium on alumina. The reactor has a ratio of height/diameter of 8:1 and operates at a temperature of 80° C. with a pressure of 3 kg/cm. By operating with an LHSV of 3, the overhead mixture leaving the reactor top has the following composition:

| | |
|---|---|
| * paraffin | 85.2% |
| * monoolefin | 12.3% |
| * diolefin | not measurable |
| * aromatics | 2.5% |

Such a mixture is sent to the alkylation reactor so as to have, under steady-state conditions, at a reaction temperature of 50° C., the following composition in the reactant system: paraffin-olefin-aromatics mixture 67.5 parts

| | |
|---|---|
| * paraffin-olefin-aromatics mixture | 67.5 parts |
| * benzene | 32.5 parts |
| * $AlCl_3$ | 0.1 parts |
| * high-boiling alkylates | 2.0 parts |
| * hydrocarbonaceous catalytic complex | 2 | wherein the total amount of water added together with the reactants is 0.002 parts.

Upon leaving the reactor, the mixture is treated as disclosed in Example 1, and, after the excess of benzene and the paraffins being separated, an overhead distilled stream of linear alkylbenzene product is obtained which displays the following characteristics:

| | |
|---|---|
| n-phenyl-$C_{10}$-$C_{13}$'s = | 97.0% |
| tetralins = | <0.5% |
| iso alkyl benzenes = | 2.3% |
| 2-phenylisomers $C_{10}$–$C_{13}$ = | 30.1% |
| bromine number = | 18 mg of Br/100 g |
| chlorine = | 7 ppm |

The heavy alkylated product separated on the bottom of the distillation tower displays the following composition:

| | |
|---|---|
| G.C.: residual LAB: | 1.2% |
| Mass-analysis: | |
| * alkyl-polyalkylbenzenes: | 93.1% |
| * diphenylalkanes-acenaphthenes: | 2.6% |
| * naphthalenes: | 1.3% |
| * tetralins-indanes: | 3.0% |
| Molecular weight = | 327.5 |

Under steady-state conditions, from the alkylation the following mass balance data are obtained:

155 parts of heavy alkylates per 1000 parts of charged LAB.

The overall data relevant to the whole production process, relatively to the production of 1000 parts of LAB are as follows:

868 parts of paraffin 352 parts of benzene 8 parts of $AlCl_3$

EXAMPLE 4

The olefin-paraffin mixture, having the same composition as disclosed at Example 3, is sent to the alkylation reactor after being mixed with benzene, so that under steady-state conditions at 65° C., the following composition of the reaction system is obtained:

| | |
|---|---|
| * olefin-paraffin-aromatics mixture | 67.5 parts |
| * benzene | 40 parts |
| * $AlCl_3$ | 0.12 parts |
| * high-boiling alkylates | 4.0 parts |
| * Hydrocarbonaceous catalytic complex | 4.0 parts | wherein the total amount of water added together with the reactants is 0.005 parts.

Upon leaving the reactor, the mixture is treated as disclosed in Example 1, and, after the excess of benzene and the paraffins being separated, an overhead distilled stream of linear alkylbenzene product is obtained which displays the following characteristics:

| G.C. | |
|---|---|
| n-phenyl-$C_{10}$—$C_{13}$'s = | 96.6% |
| 2-phenylisomer = | 30.0 |
| tetralins = | 0.7% |
| iso alkyl benzenes = | 2.5% |
| bromine number = | 20 mg of Br/100 g |
| chlorine = | 10 ppm |

The heavy alkylated product separated at the bottom of the distillation tower displays the following composition:

| G.C.: residual LAB: | 3.0% |
|---|---|
| Mass analysis: | |
| * alkyl-polyalkylbenzenes: | 91.8% |
| * diphenylalkanes-acenaphthenes: | 2.9% |
| * naphthalenes: | 1.4% |
| * tetralins-indanes: | 3.9% |
| Molecular weight = | 388.5 |

Under steady-state conditions, from the alkylation the following mass balance data are obtained:

52 parts of heavy alkylates per 1000 parts of charged LAB.

The overall balance data relevant to the whole process of dehydrogenation of the paraffins, of selective hydrogenation of the diolefins and of benzene alkylation, relevant to the production of 1000 parts of LAB, are the following:

788 parts of paraffin 330 parts of benzene 10 parts of $AlCl_3$

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Integrated process for preparing linear alkylbenzenes having 10–14 carbon atoms in the alkyl chain from a feed including aromatic hydrocarbons with n-paraffins, said process comprising the steps of:

(a) dehydrogenating n-paraffins to corresponding n-olefins;

(b) selectively hydrogenating diolefins formed during the preceding step to convert them into mono-olefins, thus forming a reaction mixture including olefins and paraffins;

(c) alkylating benzene in said reaction mixture of olefins and paraffins in the presence of an active catalytic species based on $AlCl_3$ so as to form an alkylated benzene mixture;

(d) forming a hydrocarbonaceous catalytic complex between said $AlCl_3$ catalytic species and the alkylated benzene mixture;

(e) separating said hydrocarbonaceous catalytic complex from said alkylated benzene;

(f) adding an additional quantity of $AlCl_3$ to said hydrocarbonaceous catalytic complex;

(g) recycling said $AlCl_3$ hydrocarbonaceous catalytic complex to step (c).

2. Integrated process for preparing linear alkylbenzenes having 10–14 carbon atoms in the alkyl chain from a feed including aromatic hydrocarbons with n-paraffins, said process comprising the steps of:

(a) dehydrogenating n-paraffins to corresponding n-olefins;

(b) separating hydrogen and light hydrocarbons from the dehydrogenated product of step (a);

(c) either before or after step (b), selectively hydrogenating diolefins formed during step (a) to convert them into mono-olefins, thus forming a reaction mixture including olefins and paraffins;

(d) adding benzene to said reaction mixture;

(e) alkylating benzene in said reaction mixture of olefins and paraffins in the presence of an active catalytic species based on $AlCl_3$ so as to form an alkylated benzene mixture;

(f) forming a hydrocarbonaceous catalytic complex between said $AlCl_3$ catalytic species and the alkylated benzene mixture;

(g) separating said hydrocarbonaceous catalytic complex from said alkylated benzene;

(h) adding an additional quantity of $AlCl_3$ to said hydrocarbonaceous catalytic complex;

(i) recycling said $AlCl_3$ hydrocarbonaceous catalytic complex to step (e).

3. Process for preparing linear alkylbenzenes according to claim 2, wherein the alkylating step (c) is carried out in the presence of an amount of $AlCl_3$ which ranges from 0.05 to 10 mol %, based on n-olefin.

4. Process for preparing linear alkylbenzenes according to claim 2, wherein the alkylating step (c) is carried out at a molar ratio of benzene:n-olefins within the ranges of from 1:1 to 20:1.

5. Process for preparing linear alkylbenzenes according to claim 2, wherein the alkylating step (c) is carried out at a temperature within the range of from 20° to 80° C.

6. Process for preparing linear alkylbenzenes according to claim 2, wherein the alkylating step (c) is carried out under a pressure within the range of from 1 to 5 $kg/cm^2$.

7. Process for preparing linear alkylbenzenes according to claim 4 wherein the molar ratio of benzene:n-olefins is from 3:1 to 15:1.

8. Process for preparing linear alkylbenzenes according to claim 2, further comprising recovering high boiling polyalkylate having a molecular weight greater than 320 with a substantial fraction of dialkylates having a molecular weight greater than 360.

9. Process for preparing linear alkylbenzenes according to claim 2, wherein a substantial quantity of 2-phenyl isomers are formed.

10. Integrated process for selectively preparing substantially pure $C_{10}$–$C_{14}$ alkylbenzenes from a feed including aromatic hydrocarbons with n-paraffins, said process comprising the steps of:

dehydrogenating n-paraffins to corresponding n-olefins in a dehydrogenation zone;

selectively hydrogenating diolefins formed during said dehydrogenating step so as to substantially eliminate diolefins and to form an olefin and paraffin mixture;

admixing said olefin and paraffin mixture in an alkylation zone with benzene in the presence of $AlCl_3$ and under alkylation conditions, whereby said benzene is alkylated;

forming a hydrocarbonaceous catalytic complex between said $AlCl_3$ and the alkylated benzene wherein said hydrocarbonaceous catalytic complex is subsequently separated from the alklated benzene and recycled to said alkylation zone;

separating unreacted paraffins from the alklated benzene;

recycling the separated unreacted paraffins to said dehydrogenation zone wherein, due to the substantial elimination of said diolefins in said hydrogenating step and the presence of $AlCl_3$, the n-paraffins being substantially free of aromatic compounds which boil at a temperature lower than the boiling point of said $C_{10}$–$C_{14}$ alkylbenzenes;

distilling the alkylated benzene mixture so as to separate said $C_{10}$–$C_{14}$ alkylbenzenes from other alkylated species.

* * * * *